United States Patent [19]

Kodama

[11] Patent Number: 5,037,200
[45] Date of Patent: Aug. 6, 1991

[54] LASER-OPERATED DETECTOR

[75] Inventor: Nobuhiro Kodama, Kanagawa, Japan

[73] Assignee: Tosoh Corporation, Yamaguchi, Japan

[21] Appl. No.: 547,359

[22] Filed: Jul. 3, 1990

[30] Foreign Application Priority Data

| Jul. 11, 1989 | [JP] | Japan | 1-177204 |
| Jul. 11, 1989 | [JP] | Japan | 1-177205 |
| Jul. 11, 1989 | [JP] | Japan | 1-177206 |
| Jul. 11, 1989 | [JP] | Japan | 1-177207 |
| Jul. 11, 1989 | [JP] | Japan | 1-177208 |

[51] Int. Cl.$^5$ .............................................. G02B 23/10
[52] U.S. Cl. ................................. 356/252; 372/20; 372/41
[58] Field of Search .............. 372/20, 41; 356/252, 356/338, 339

[56] References Cited

U.S. PATENT DOCUMENTS 4,836,953  6/1989  Kokta ................................. 372/20

FOREIGN PATENT DOCUMENTS 0238142  3/1987  European Pat. Off. .

Primary Examiner—Léon Scott, Jr.
Attorney, Agent, or Firm—Sughrue, Mion, Zinn, Macpeak & Seas

[57] ABSTRACT

In a laser-operated detecting device, the light source of a laser beam applied to a specimen under test is a tunable laser whose wavelength can be continuously tuned in a certain range. The detecting device is realized as a high speed liquid chromatography fluorescence detector, a high speed liquid chromatography Raman detector, a laser Raman spectroscopic measuring device, a coherent anti-Stokes Raman measuring device, or a microscopic Raman measuring device.

10 Claims, 3 Drawing Sheets

LASER-OPERATED DETECTOR

BACKGROUND OF THE INVENTION

This invention relates to a detector with a titanium sapphire laser as a pumping light source the laser beam of which can be continuously changed in wavelength.

There have been proposed a variety of detecting or measuring devices based on an optical method for instance in the field of analysis.

Examples of the detecting or measuring devices are a high speed liquid chromatography fluorescence detector, and a variety of Raman measuring devices. These detecting or measuring devices have been widely employed as means for quantitatively analyzing biological specimens such as physiological active substances with high accuracy, means for studying the structures of biological substances, means for analyzing the crystalline configurations of solid substances, and so forth for instance in the field of medicine or in the field of biochemistry.

It is practically essential for the above-described detecting or measuring devices based on the optical method to have an exciting light source which is capable of emitting a light beam whose wavelength matches the responsive wavelength band of a component under test. Most of the commercially available lasers are so designed as to emit laser beams having wavelengths which are inherent in them, respectively. Examples of such lasers are an Ar laser (488, 515 nm), He-Ne laser (633 nm) and copper vapor laser (511 nm) provided as gas lasers, and a YAG laser (1064 nm) and a semiconductor laser (780, 830, 1300, 1550 nm) provided as solid lasers.

However, these lasers are not always practical in use. The Ar, He-Ne, copper vapor and YAG lasers are discrete or discontinuous as was described above. Hence, if, in the case where any one of these lasers is employed as a light source, the response wavelength of a component under test is different from the wavelength of the laser beam, then the component cannot be tested. Even if it could be tested, the test would be considerably low in sensitivity. The same thing can be said to a semiconductor laser whose wavelength can be changed in a range of several nanometers (nm).

A dye laser is variable in oscillation wavelength, and its wavelength can be matched with the response wavelength band of a component under test. However, the dye laser is disadvantageous in that the dye is deteriorated by light during operation, so that the laser oscillation output is varied; that is, the dye laser is unstable in operation, and furthermore the dye laser is relatively short in service life, and its maintenance is rather difficult.

Frequently, the absorption spectrum of a specimen is different from the wavelength of the laser. Accordingly, in the case where such a laser beam source discrete in oscillation wavelength is employed for a detecting device such as a high speed liquid chromatography fluorescence detector, it would be difficult to perform even an analysis of the order of pico-grams. Therefore when it is forced to perform the analysis with high sensitivity, analysis, intricate operations must be carried out; for instance in measurement of a fluorescent spectrum, the specimen must be made fluorescent by chemical treatment. Even if the specimen is made fluorescent, it is difficult to give a high sensitivity analysis of the order of "femto ($10^{-15}$) grams" to it. From the spectrum of the output light of an Xe lamp, light is obtained in a wide range of from about 220 nm to about 1000 nm; however, the light is weaker than the laser beam, and accordingly it is difficult to perform a high sensitivity quantitative analysis with the output light of the Xe lamp.

In the case of a Raman measuring device incorporating such a laser, it is difficult to stably and readily measure the Raman spectrum of a specimen under test at all times.

Thus, the conventional devices suffer from various problems.

SUMMARY OF THE INVENTION

In view of the foregoing, it is an object of this invention to provide a laser-operated detecting device with which the spectrum of a specimen under test can be detected selectively, stably and readily.

The foregoing object and other objects of the invention have been achieved by the provision of a laser-operated detecting device which, according to the invention, employs a titanium-added sapphire as a wavelength variable laser beam source. The detecting device is realized as a high speed liquid chromatography fluorescence detector, a high speed liquid chromatography Raman detector, a laser Raman measuring device, a coherent anti-Stokes Raman measuring device, or a microscopic Raman measuring device.

The nature, principle and utility of the invention will become more apparent from the following detailed description when read in conjunction with the accompanying drawings.

DETAILED DESCRIPTION OF THE INVENTION

The present inventor has conducted intensive research on a laser-operated detecting device based on an optical method to eliminate the above-described difficulties, and found that the difficulties can be eliminated by using a titanium-doped sapphire (in which a titanium is added to a sapphire as a dopant, so-called "titanium sapphire element", as a light source for a tunable laser.

In a laser-operated detecting device according to the invention, the light source of a laser beam applied to a specimen under test is a tunable laser whose wavelength can be continuosly tuned in a certain range. The laser as used herein is a titanium sapphire laser with a titanium-doped sapphire. It is preferable that the amount of addition of titanium to sapphire is in a range of 0.01 atomic % to 0.5 atomic %. If the amount of titanium is less than 0.01 atomic %, the degree of amplification is small, as a result of which the laser oscillation is difficult. If the amount of addition of titanium is more than 0.5 atomic %, then the residual absorption in the light emission region is extremely increased, as a result of which the laser oscillation efficiency is decreased.

A typical example of the arrangement of a light source section in the detecting device according to the invention is as follows: The light of a pumping light source is applied to a titanium sapphire which forms a part of the specific feature of the invention, to oscillate it, and it is further applied through a harmonic generation section to a tuning section, or it is applied directly to the tuning section. The light source section may be so modified that the light is applied through the tuning section to the higher harmonic generating section.

In the invention, the use of the titanium sapphire laser and the harmonic generation section with a nonlinear optical material in combination, the response wavelength band of a specimen under test can be detected in a wide range of from 330 nm to 550 nm and from 660 nm to 1100 nm. This contributes to the provision of a laser-operated detecting device higher in detection accuracy.

The non-linear optical material employed in the invention is a crystal of β-barium borate or lithium niobate, or methanitroaniline, which can double the wavelength of light.

Preferred embodiments of this invention will be described with reference to the accompanying drawings.

Figure 1:
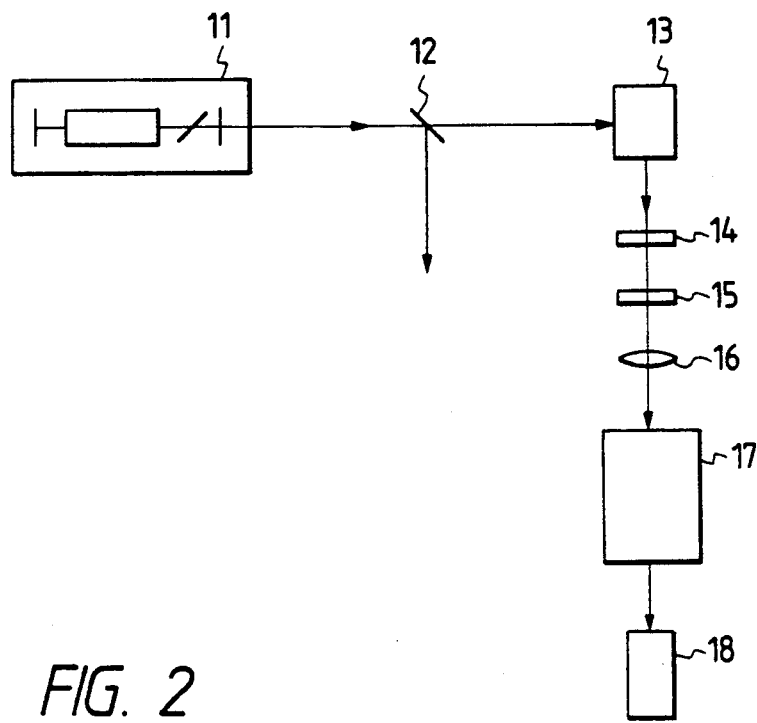
FIG. 1 is an explanatory diagram outlining the arrangement of a high speed liquid chromatography fluorescence or Raman detector, a first embodiment of this invention.

FIG. 1 shows the arrangement of a high speed liquid chromatography fluorescence or Raman detector, a first embodiment of this invention. In FIG. 1, reference numeral 11 designates a titanium sapphire laser oscillator; 12, a half-mirror; 13, a specimen cell; 14, a polarizer; 15, a non-polarizing plate lens; 16, a condenser lens; 17, a spectroscope; and 18, a detecting element such as a photo-multiplier bulb.

Figure 2:
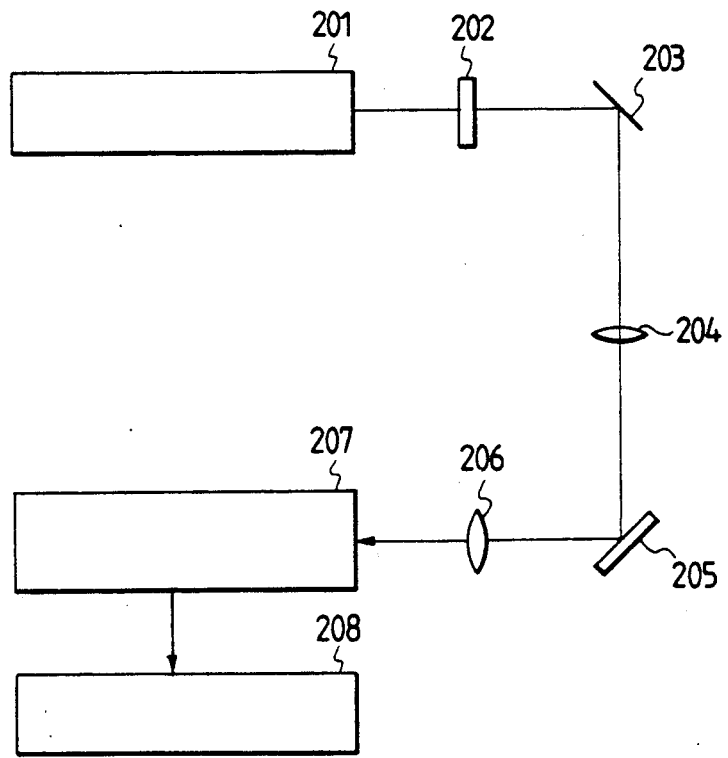
FIG. 2 is an explanatory diagram outlining the arrangement of a laser Raman measuring device, a second embodiment of the invention.

FIG. 2 shows the arrangement of a laser Raman measuring device, a second embodiment of the invention. In FIG. 2, reference numeral 201 designates a titanium sapphire laser oscillator 202, an interference filter; 203, a reflecting mirror; 204, a focusing lens; 205, a specimen; 206, a condenser lens; 207, a spectroscope; and 208, a detecting element.

Figure 3:
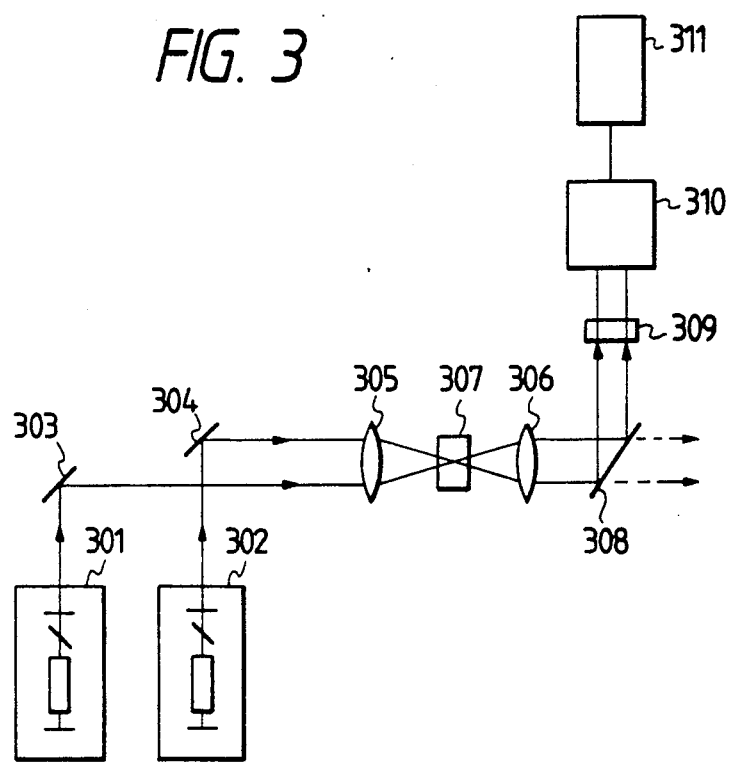
FIG. 3 is an explanatory diagram outlining the arrangement of a coherent anti-Stokes Raman measuring device, a third embodiment of the invention.

FIG. 3 shows the arrangement of a coherent anti-Stokes Raman measuring device, a third embodiment of the invention. In FIG. 3, reference numerals 301 and 302 designate titanium sapphire laser oscillators; 303 and 304, reflecting mirrors; 305 and 306; lenses; 307, a specimen; 308, a dichroic mirror; 309, a filter; 310, a monochromator; and 311, a detecting element.

Figure 4:
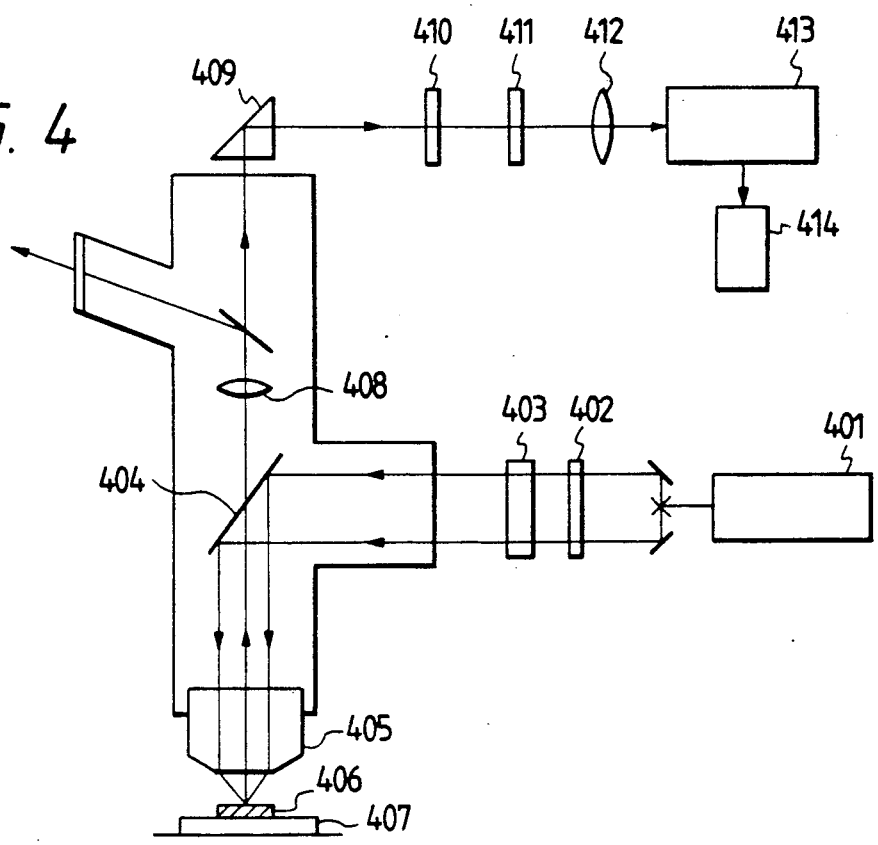
FIG. 4 is an explanatory diagram outlining the arrangement of a microscopic Raman measuring device, a fourth embodiment of the invention.

FIG. 4 outlines the arrangement of a microscopic Raman measuring device, a fourth embodiment of the invention. In FIG. 4, reference numeral 401 designates a titanium sapphire laser oscillator; 402, an aperture; 403, a polarization rotor; 404, a beam splitter; 405, an objective lens; 406, a specimen; 407, an X-Y stage; 408, a lens; 409, a prism; 410, a polarizer; 411, depolarizing plate; 412, a lens; 413, a spectroscope; and 414, a detecting element.

The arrangement of the detecting or measuring device according to the invention is not always limited to those which have been described above. The non-linear optical material may be disposed between the titanium sapphire laser oscillator and the specimen. Examples of a source for pumping the titanium sapphire crystal which is a laser medium are a flash lamp, the second harmonic of YAG laser, dye laser, argon laser, copper vapor laser, light emitting diode, and semiconductor laser; however, the invention is not limited thereto or thereby. That is, the pumping source may be means for emitting light beams having wavelengths which effectively give energy to the light absorbing band of the titanium sapphire crystal.

The tuning of the wavelength can be achieved for instance with a prism, bi-refringent filter, diffraction grating, electro-optic crystal device, or acousto-optic crystal device.

Figure 5:
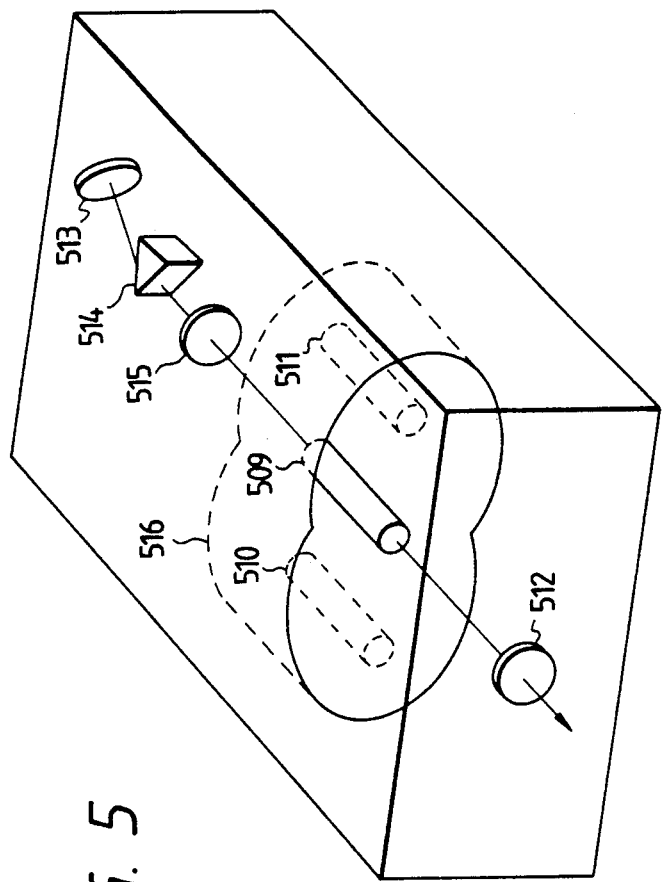
FIG. 5 is an explanatory diagram outlining the arrangement of one example of a flash-lamp-excited laser oscillator.

FIG. 5 outlines one example of a flash-lamp-excited laser oscillator. In FIG. 5, reference numeral 509 designates a titanium sapphire rod; 510 and 511, flash lamps; 512 and 513, reflecting mirrors; 514, a prism; 515, an etalon; and 516, an elliptic light concentrating mirror. A silver film is preferably formed on the light reflecting surface of the light concentrating mirror by vacuum deposition to improve the efficiency of reflection of the sapphire pumping light.

Figure 6:
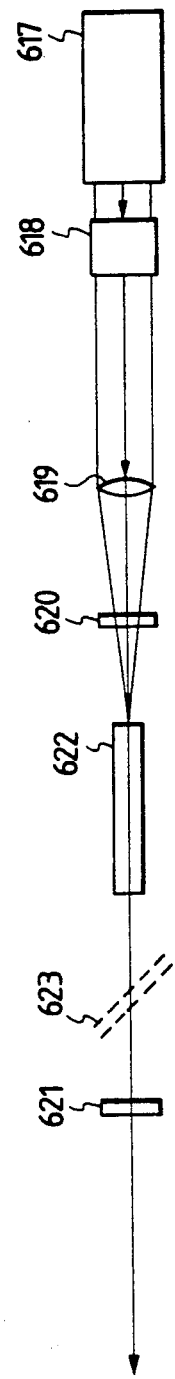
FIG. 6 is an explanatory diagram outlining the arrangement of a sapphire laser oscillator which is pumped with the second harmonic of a YAG laser, in a high speed liquid chromatography detector.

FIG. 6 is a diagram outlining the arrangement of one example of a sapphire laser oscillator which is excited with the second harmonic of the YAG laser, in a high speed liquid chromatography detector. In FIG. 6, reference numeral 617 designates a YAG laser; 618, a crystal of non-linear optical material; 619, a condenser lens; 620 and 621, reflecting mirrors; 622, a titanium sapphire rod; and 623, a bi-refringent filter.

The wavelength of the laser beam can be tuned continuously in a range of from about 660 nm to about 1100 nm according to the above-described method.

In the case where the second harmonic is generated with the nonlinear optical material, the wavelength of the laser beam can be emitted in a range of from about 330 nm to about 550 nm; and in the case where the third harmonic is produced, it can be changed in a range of from about 220 nm to about 360 nm.

As is apparent from the above description, with the device according to the invention, the wavelength of the laser beam can be selected in a wide range, and accordingly the number of kinds of specimens which can be detected is increased as much. As for a substance having its absorption spectrum in that range, the wavelength of the laser beam can be made equal to the absorption pumping wavelength with ease, and accordingly for instance a spectrum measurement can be achieved with high accuracy. That is, the measurement sensitivity is improved, and even a specimen low in concentration can be measured substantially effectively.

The titanium sapphire laser can produce not only a continuous laser beam but also a pulse laser beam. With a picosecond pulse laser beam, the measurement can be achieved with high time resolution.

In the invention, the probe light beam can be continuously changed by using the titanium sapphire laser, and therefore for instance the spectrum of a specimen can be measured with high selectivity, with high sensitivity and with high time resolution. In addition, the measurement can be readily achieved with high stability. Furthermore, the device is simple in construction, and its maintenance can be achieved with ease.

While there has been described in connection with the preferred embodiments of this invention, it will be obvious to those skilled in the art that various changes and modifications may be made therein without departing from the invention, and it is aimed, therefore, to cover in the appended claims all such changes and modification as fall within the true spirit and scope of the invention.

What is claimed is:

1. In a detector device, a tunable laser source emitting a light beam whose wavelength matches a responsive wavelength band of a specimen under test, said tunable laser source comprising:
   a titanium-doped sapphire laser having continuously variable wavelength capability.

2. A detecting device as claimed in claim 1, in which the amount of doped titanium in sapphire is in a range of 0.01 atomic % to 0.5 atomic %.

3. A detecting device as claimed in claim 1, in which said tunable solid laser is made up of a titanium-doped sapphire and a non-linear optical material.

4. A detecting device as claimed in claim 3, in which the amount of doped titanium in sapphire is in a range of 0.01 atomic %, to 0.5 atomic %.

5. A detecting device as claimed in claim 3, in which said non-linear optical material is selected from the group comsisting of a β-barium borate, lithium niobate and methanitroaniline.

6. A detecting device as claimed in claim 1 or 3, in which said detecting device is a high speed liquid chromatography fluorescence detector.

7. A detecting device as claimed in claim 1 or 3, in which said detecting device is a high speed liquid chromatography Raman spectra detector.

8. A detecting device as claimed in claim 1 or 3, in which said detecting device is a laser Raman spectro scopic measuring device.

9. A detecting device as claimed in claim 1 or 3, in which said detecting device is a coherent anti-Stokes Raman measuring device.

10. A detecting device as claimed in claim 1 or 3, in which said detecting device is a microscopic Raman measuring device.

* * * * *